United States Patent [19]

Noltes et al.

[11] 4,243,604
[45] Jan. 6, 1981

[54] ALIPHATIC METAL CLUSTER COMPOUNDS

[75] Inventors: Jan G. Noltes, Huis ter Heide; J. T. B. H. Jastrzebski, De Bilt; Gerard van Koten, Bilthoven, all of Netherlands

[73] Assignee: Borg-Warner Corporation, Chicago, Ill.

[21] Appl. No.: 18,373

[22] Filed: Mar. 7, 1979

[51] Int. Cl.$^3$ ............................................. C07F 1/12
[52] U.S. Cl. ............................... 260/430; 252/431 L; 260/438.1
[58] Field of Search ............................... 260/430, 438.1

[56] References Cited

U.S. PATENT DOCUMENTS

| | | | |
|---|---|---|---|
| 3,475,471 | 10/1969 | Maxfield | 260/430 X |
| 3,661,959 | 5/1972 | Vaughan | 260/430 |
| 3,700,693 | 10/1972 | Cairncross et al. | 260/438.1 X |
| 3,798,248 | 3/1974 | van Koten et al. | 260/438.1 X |

OTHER PUBLICATIONS

Tamaki et al., JACS 96 6140–6148, (1974).
JACS 94, 7210–7211, (1972).
House et al., J. Org. Chem. 40 (10), pp. 1460–1469, (1975).
Chemical Abstracts 71 50163s, (1969).
Chavdarian et al., JACS 97, 3822–3823, (1975).
J. Organometallic Chemistry 95, 340–352, (1975).
Chemical Abstracts 73 35485w, (1970).
Chemical Abstracts, 9th Collective Index, vols. 76–85, (1972–1976).
Chemical Abstracts, 80 83170f, (1974).

*Primary Examiner*—Helen M. S. Sneed
*Attorney, Agent, or Firm*—Joseph Shekleton

[57] ABSTRACT

A process for the preparation of novel aliphatic metal cluster compounds. The cluster compounds are prepared by reacting an alkyllithium such as n-butyllithium with a Group Ib metal halide or Group Ib metal halide complex such as gold chloride.triphenyl-phosphine. The resulting cluster compound is relatively stable.

7 Claims, No Drawings

ALIPHATIC METAL CLUSTER COMPOUNDS

The invention of this application relates to a process for the preparation of novel aliphatic metal cluster compounds. The metal cluster compounds are useful as starting materials in the preparation of zero-valent metal catalysts which are effective to catalyze the hydrogenation of aromatic, olefinic and acetylenic compounds. These zero-valent metal compounds are also useful in the catalysis of dehydrogenation reactions.

Ten Hoedt et al., J. Organomet. Chem. 133 (1977) 113–121, show the preparation of certain mixed-organocopper cluster compounds by the liguand substitution reaction of $Ar_4Cu_6Br_2$ with two equivalents of LiC-CR.

Van Koten et. al., J. Organomet. 85(1)(1975) 105–114, propose an organic copper cluster structure which is polymeric in nature.

The preparation of aromatic metal cluster compounds and their use in preparation of zero-valent metal compounds having catalytic properties is shown in copending application Ser. No. 827,278, filed Aug. 24, 1977, now U.S. Pat. No. 4,152,303.

Tamaki et al., J. Organomet. Chem. 51 (1973) 39–42, show the preparation of the triphenylphosphite complex of dimethylgoldlithium by the reaction of the triphenylphosphite complex of methyl gold with methyllithium. The product is said to be unstable, decomposing when removed from an ethereal environment at $-80°$ C.

Rice et al., Inorg. Chem., 14, No. 10 (1975) 2402–7, show certain NMR spectral data for the dimethylgoldlithium complex above.

The invention of the present application is a process for the preparation of an aliphatic metal cluster compound of the formula $R_{x+y}M_xLi_y$ where R is alkyl of 3–12 carbon atoms, M is a group Ib metal, x and y are each 1–4 and x+y is 2–8, comprising reacting an alkyllithium wherein the alkyl group contains 3–12 carbon atoms, with a metal halide MX or metal halide complex MXL wherein M is a Group Ib metal, X is chlorine or bromine, and L is an organic ligand, in a hydrocarbon solvent. The invention also includes the aliphatic metal cluster compound thus prepared. The process preferably is carried out in a dry-oxygen-free atmosphere. The atmosphere may be, e.g., nitrogen, ethylene or argon.

The alkyllithium reactant may, as indicated, be one wherein the alkyl contains 3–12 carbon atoms. Illustrative examples include n-propyl, isopropyl, n-butyl, isobutyl, 2-butyl, tert-butyl, 1-pentyl, 2-pentyl, isopentyl, n-hexyl, n-heptyl, 2-ethylhexyl, isooctyl, n-decyl, isodecyl and n-dodecyl.

The metal (M) in the metal halide complex may be any Group Ib metal including copper, silver and gold, although gold is preferred. The halogen (X) may be either chlorine or bromine. The organic ligand (L) is construed broadly; specific illustrative embodiments include ethylene, 1-butene, 1,5-cyclooctadiene, 1,4-norbornadiene, 1-hexene, triphenylphosphine, carbon monoxide and diethyl ether. Olefinic hydrocarbons having up to 12 carbon atoms are preferred. Examples of suitable metal halides and metal halide complexes include copper bromide, silver chloride 1,5-cyclooctadiene ($AgCl.C_8H_{12}$), gold chloride.triphenylphosphine ($AuCl.PPh_3$), gold chloride.carbon monoxide ($AuCl.CO$) and gold bromide.diethyl ether ($AuBr.C_2H_5OC_2H_5$).

The metal cluster compounds herein are relatively insoluble in hydrocarbon solvents. Their solubility is increased considerably by converting them to complexes with ethers. Dialkyl ethers, and diethyl ether particularly, are well suited for this purpose. The relative solubility of the diethyl ether complex of a metal cluster compound permits its analysis by $'H$-NMR; it also facilitates the reaction of the metal cluster compound with various transition metal halide complexes to form products which are effective hydrogenation catalysts.

Preparation of the ether complexes involves merely carrying out the process of preparing the metal cluster compound in ether solution, or mixing the metal cluster compound with at least an equivalent amount of ether.

Although the aliphatic metal cluster compounds herein are surpisingly stable, care should be taken to prevent their hydrolysis and decomposition by hydrolysis or oxidation. As noted earlier, their preparation preferably is carried out under anhydrous and oxygen-free conditions.

The process is carried out very simply, merely by mixing the reactants at room temperature, i.e., from about 20° C. to about 30° C. Temperature is not a critical feature of the process and lower or higher temperatures may be used depending, for the most part, on the particular reactants which are used. A reaction occurs almost immediately resulting in formation of the desired aliphatic metal cluster compound and lithium halide, which latter precipitates from solution.

The process is carried out in a solvent. The Group Ib metal halide complex may not be completely soluble in the solvent, and agitation of the process mixture is, therefore, advisable. Suitable solvents include benzene, toluene, xylene, ethylbenzene, pentane, cyclohexane and, in fact, any hydrocarbon solvent which is normally liquid, i.e., liquid at about room temperature.

The process of the invention is illustrated by the following example.

EXAMPLE

To a stirred suspension of 4.94 g. (10.0 mmols) of gold chloride.triphenylphosphine complex ($AuCl.PPh_3$) in 100 ml. of n-pentane and 1.11 g. (15 mmols) of diethyl ether there is added 1.28 g. (20.0 mmols) of n-butyllithium. The reaction mixture develops a yellow color and a white precipitate forms. The mixture is chilled to $-80°$ C. and the yellow liquid is decanted from the solid; the solid is identified by its $'H$-NMR spectrum in $C_6D_6$ as triphenylphosphine. The yellow pentane solution is evaporated at 50° C/0.1 mm. Hg, yielding a yellow-brown oil. Its $'H$-NMR spectrum in $C_6D_6$ shows butyl and ether signals in a 2:1 ratio, which is consistent with the structure of the organic metal cluster compound $n-Bu_2AuLi.Et_2O$. This product is thus isolated in a 98% yield. It is sensitive to hydrolysis and oxidation.

As noted earlier herein, the aliphatic metal cluster compounds of the invention are useful in the preparation of zero-valent metal compounds which are in turn useful as catalysts in hydrogenation reactions. The metal cluster compounds can be reacted with transition metal halide complexes to give the desired zero-valent products. Thus, the di-n-butylgoldlithium etherate prepared by the procedure of the above example can be reacted with rhodium chloride ethylene complex $RhCl.(CH_2=CH_2)_2$ to give a zero-valent mixed metal product ($Au°/Rh°$) which is effective to catalyze the hydrogenation of benzene at room temperature and atmospheric pressure, at a rate of 1.6 mol/min/ mmol of catalyst.

All parts and percentages herein, unless otherwise expressly stated, are by weight.

We claim:

1. A process for the preparation of an aliphatic metal cluster compound of the formula $R_{x+y}Au_xLi_y$ where R is alkyl of 3–12 carbon atoms, x and y are each 1–4 and x+y is 2–8, comprising reacting an alkyllithium wherein the alkyl group contains 3–12 carbon atoms, with AU or AUMXL wherein, X is chlorine or bromine, and L is an organic ligand, in a hydrocarbon solvent.

2. The process of claim 1 wherein the alkyl group of the alkyllithium is a butyl group.

3. The process of claim 1 wherein the alkyl group of the alkyllithium is an n-butyl group.

4. The process of claim 1 wherein the alkyllithium and AUX or AUXH are mixed in an ether solvent.

5. The process of claim 1 wherein the organic ligand L is an olefinic hydrocarbon.

6. The process of claim 1 wherein the organic ligand L is ethylene.

7. An aliphatic metal cluster compound having the formula $$R_{x+y} AU_xLi_y$$

where R is alkyl of 3–12 carbon atoms, x and y are each 1–4, and x+y is 2–8, and etherates thereof.

* * * * *